(12) United States Patent
Frigg et al.

(10) Patent No.: US 8,167,909 B2
(45) Date of Patent: May 1, 2012

(54) CONNECTING ELEMENT

(75) Inventors: Robert Frigg, Bettlach (CH); Bruno Läng, Horriwil (CH)

(73) Assignee: Synthes USA, LLC, West Chester, PA (US)

( * ) Notice: Subject to any disclaimer, the term of this patent is extended or adjusted under 35 U.S.C. 154(b) by 1032 days.

(21) Appl. No.: 11/497,743

(22) Filed: Aug. 1, 2006

(65) Prior Publication Data

US 2007/0042633 A1  Feb. 22, 2007

Related U.S. Application Data

(63) Continuation of application No. PCT/CH2004/000129, filed on Mar. 4, 2004.

(51) Int. Cl.
*A61B 17/70* (2006.01)
(52) U.S. Cl. .................. 606/254; 606/255; 606/60
(58) Field of Classification Search .............. 606/61, 606/246, 250–265; 411/57.1, 58, 59, 80.5–80.6, 411/291, 405, 418, 529
See application file for complete search history.

(56) References Cited

U.S. PATENT DOCUMENTS

| | | | |
|---|---|---|---|
| 4,653,132 A * | 3/1987 | Yamada | 470/14 |
| 5,643,261 A * | 7/1997 | Schafer et al. | 606/250 |
| 2003/0220642 A1 | 11/2003 | Freudiger | 606/61 |
| 2004/0215191 A1 * | 10/2004 | Kitchen | 606/61 |
| 2006/0195093 A1 * | 8/2006 | Jahng | 606/61 |

FOREIGN PATENT DOCUMENTS

| | | |
|---|---|---|
| DE | 9308770 U | 8/1993 |
| FR | 2726995 A | 5/1996 |
| FR | 2743290 A | 7/1997 |
| WO | WO 94/06361 A | 3/1994 |
| WO | WO 2004/008979 A | 1/2004 |

OTHER PUBLICATIONS

Translation of the First Office Action received from Chinese Patent Office.
Japanese Patent Office: Notice of Reasons for Rejection and accompanying English translation.
Canadian Patent Application No. 2,558,419, Office Action issued Jun. 27, 2011 (2 pages).

* cited by examiner

*Primary Examiner* — Eduardo C Robert
*Assistant Examiner* — Christina Negrelli
(74) *Attorney, Agent, or Firm* — McKeon, Meunier, Carlin & Curfman, LLC

(57) ABSTRACT

The connecting element (1) has the shape of a rod with longitudinal axis (2), a rear end (6), and a front end (7), and serves to span a number of bone anchoring elements (12) implanted in the bone. The connecting element (1) comprises at least one longitudinal slot (5). This provides it with a greater elasticity during implantation so that it can be reversibly deformed. The connecting element can then be stiffened once it has been fixed in the bone anchoring elements (e.g. pedicle screws).

57 Claims, 13 Drawing Sheets

CONNECTING ELEMENT

CROSS-REFERENCE TO RELATED APPLICATIONS

This application is a continuation of International Application No. PCT/CH2004/000129, filed Mar. 4, 2004, the entirety of which is incorporated by reference herein.

FIELD OF THE INVENTION

The invention relates to a connecting element.

BACKGROUND OF THE INVENTION

Connecting elements are suitable for bridging several bone-anchoring elements, which are implanted in the bone, particularly in the region of the spinal column, that is, for bridging pedicle screws. They have been known for a long time. However, such elements are always relatively rigid longitudinal supports, which must be bent with special measures in order to adapt them to the configuration required anatomically or clinically.

The WO 02/085217 discloses a connecting element, which, instead of a single longitudinal support, consists of a plurality of elastic wires (rod bundles), lying loosely next to one another. The danger that the individual wires may cross, which would lead to unstable connections, is a disadvantage of this known device.

The invention is to provide a remedy here. It is an object of the invention to provide a connecting element, which has a greater elasticity during the implantation, so that it can be shaped reversibly, and which can be reinforced after it is fixed in the bone-anchoring elements (such as pedicle screws).

SUMMARY OF THE INVENTION

The advantages, achieved with the invention, may be seen to lie essentially therein that, due to its elasticity, the connecting element may be implanted in a minimally invasive manner through a bent tube and then stiffened by fixation with the bone-anchoring elements. In comparison to the above-mentioned, known bundle of rods, the advantage results that an accurately defined external shape is always present, that is, in the state at rest as well as in radially braced state, that is, after fixation in the bone-anchoring elements.

In the case of a particular embodiment, the connecting element has a cavity, which extends in the direction of the longitudinal axis and by means of which a sheath is defined. This permits a central rod to be introduced into the cavity. It is an advantage of such an embodiment that the slotted sheath has the same external diameter in the clamped as well as in the not clamped state. In the case of a slotted rod with a full cross section, the material losses due to the slotting must be compensated for by a reduction in the external diameter. An additional advantage lies therein that the cross section of the rod is divided among two elements, so that, as a result, the bending stiffness can be reduced.

Preferably, the slots penetrate the sheath radially and, advisably, the cavity extends continuously from the rear end to the front end, so that the connecting element is tubular.

In the case of a further embodiment, the slots are disposed in such a manner, that the sheath continues to hang together.

In the case of a further embodiment, the ends of the slots lie within the connecting element. The advantage of this embodiment lies in an increased bending stiffness of the connecting element, since the connecting element is closed at both sides and minimizes relative movement of the individual sheath elements under a bending stress.

In the case of an alternative embodiment, the ends of the slots break through the rear end and/or the front end on one side. In the case of this embodiment, there is increased bending elasticity. In the bent state of the connecting element, the radially external elements of the sheath are able to shift relatively to the radially internal elements.

The connecting element may be made from known metallic materials or from plastic.

In the case of a further embodiment, the connecting element has a circular, external cross section. As a result, the connecting element has uniform mechanical properties, independently of the orientation of the rotation of the connecting element.

In the case of an alternative embodiment, the connecting element has a polygonal, external cross section. In conjunction with pedicle screws, the rod seat of which is also constructed polygonally, a connecting element with a polygonal cross section may be oriented in a defined manner. Advantageously, the mechanical properties, such as the stiffness, may be predefined differently, depending on the direction of stress.

The slots may have a width of not more than 1.0 mm and preferably of not more than 0.6 mm.

In the case of a further embodiment, the connecting element (1) has uniform mechanical strength and stiffness over the whole of its length. The uniform stiffness of the connecting element over the whole of it length causes the bending moments applied to be distributed over the whole length of the connecting element and, by so doing, prevents stress concentrations at the transitions.

The slots may be filled at least partially with a material softer than that of the connecting element, preferably with PEEK, as a result of which undesirable growth of tissue into the connecting element is prevented.

In the case of a further embodiment, the slots, as viewed radially to the longitudinal axis, are disposed offset. A uniform bending stiffness and bending elasticity in different directions can be achieved in this way.

In the case of an alternative embodiment, several slots, when viewed axially, are disposed one behind the other, so that several radially offset groups of such slots, disposed one behind the other axially, are present. Here also, there is a uniform bending stiffness and bending elasticity in different directions. Subdividing the slots among several slots, which, viewed in the axial direction, are disposed one behind the other, is suitable especially for long connecting elements. By these means, the torsional rigidity and the bending strength may be increased and/or adapted.

In yet another embodiment, the individual slots of a group are offset axially with respect to the slots of the radially adjacent group. This results in the advantage of a uniform mechanical strength and stiffness.

In the case of a further embodiment, the connecting element additionally has a central rod, which is introduced into the cavity. This central rod may be made from a metal, preferably from titanium, a titanium alloy or steel.

BRIEF DESCRIPTION OF THE DRAWINGS

The invention and further developments of the invention are explained in greater detail in the following by means of the partially diagrammatic representations of several embodiments.

DETAILED DESCRIPTION OF THE INVENTION

Figure 1:
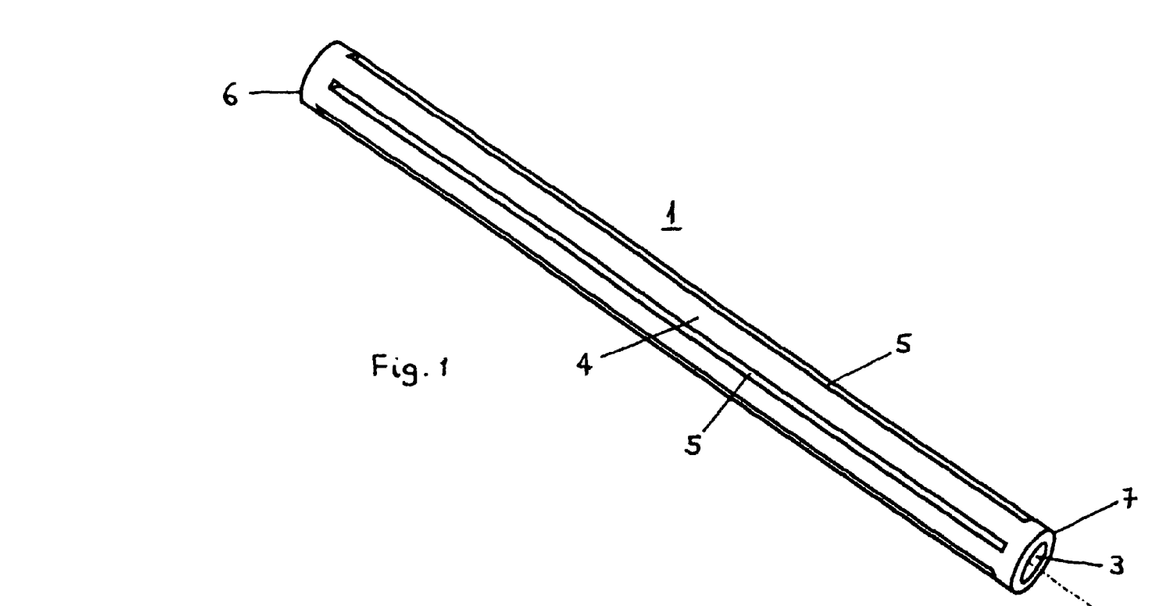
FIG. 1 shows a perspective view of an inventive connecting element.
Figure 2:
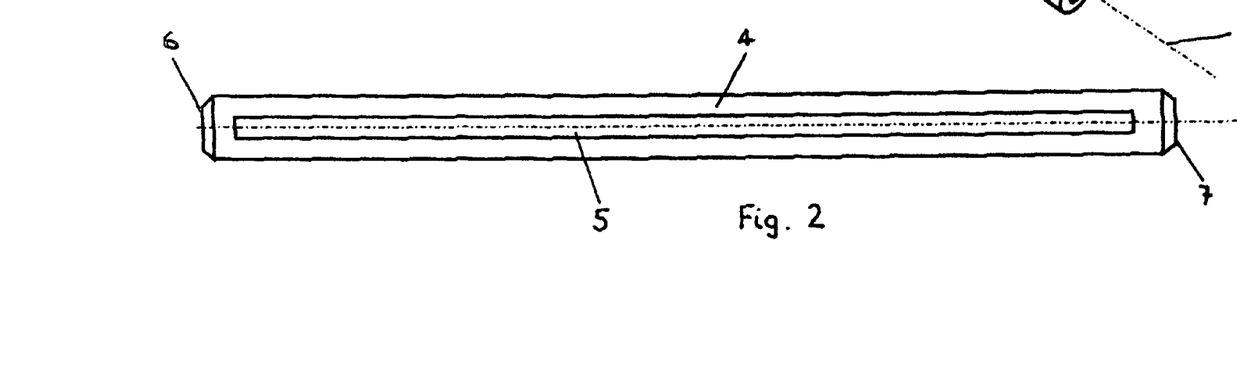
FIG. 2 shows a side view of the connecting element of FIG. 1.
Figure 3:
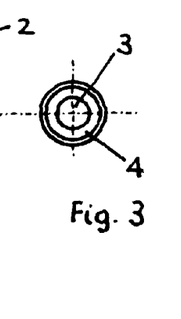
FIG. 3 shows a front view of the connecting element of FIG. 1.

An embodiment is shown in FIGS. 1 to 3, which comprises a tubular connecting element 1, with a cavity 3, which passes through the connecting element 1 from the rear end 6 up to the front end 7 and is coaxial with the longitudinal axis 2, and several longitudinal slots 5, which are distributed uniformly over the periphery of the connecting element 1 and pass radially through the sheath 4. The longitudinal slots 5 extend parallel to the longitudinal axis 2 and are closed at the two ends 6; 7 of the connecting element 1.

Figure 4:
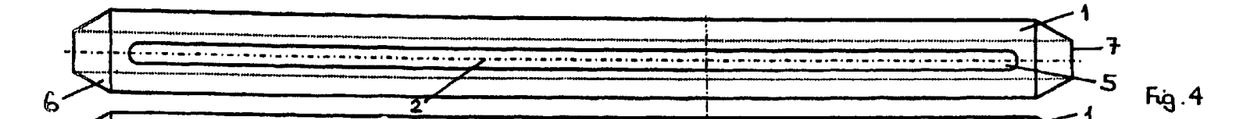
FIG. 4 shows a side view of a modified connecting element with a slot closed at either end.
Figure 5:
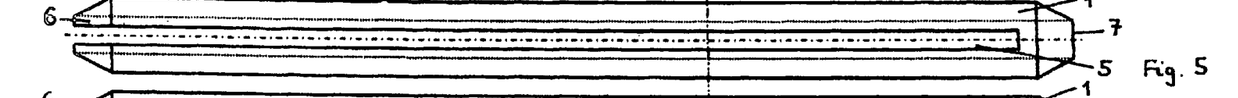
FIG. 5 shows a side view of a modified connecting element with a slot open at one side.
Figure 6:
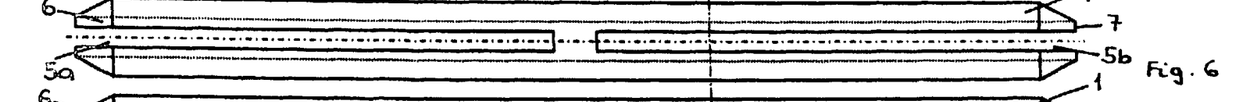
FIG. 6 shows a side view of a modified connecting element with two slots, separated by a bridge, open at one side.
Figure 7:
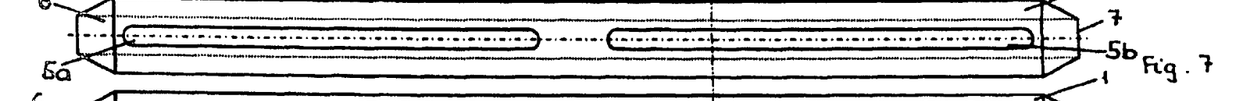
FIG. 7 shows a side view of a modified connecting element with two closed slots, separated by a bridge.
Figures 8, 9:
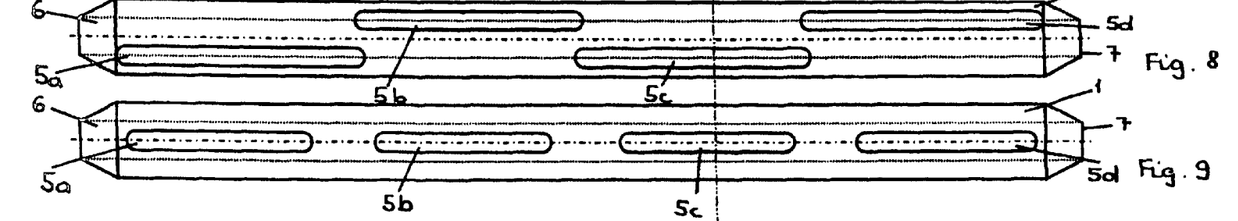
FIG. 8 shows a side view of a modified connecting element with a plurality closed slots, disposed offset to one another.
FIG. 9 shows a side view of a modified connecting element with a plurality of closed slots, which are disposed one behind the other.

Further embodiments of the connecting element 1 are shown in FIGS. 4 to 9. These differ from the embodiments of FIGS. 1 to 3 only in that the geometry and the axial arrangements of the longitudinal slot or slots 5 are different. In FIG. 4, a connecting element 1 with a longitudinal slot 5 is shown, which is closed axially at the rear end 6 as well as at the front end 7. In FIG. 5, a connecting element 1 with a longitudinal slot 5 is shown, which is open at the rear end 6 and closed at the front end 7. In FIG. 6, the connecting element 1 comprises two longitudinal slots 5a; 5b, which are separated axially from one another, and in each case one longitudinal slot 5a; 5b is open at one end 6; 7. In FIG. 7, the connecting element 1 also comprises two longitudinal slots 5a; 5b, which are disposed one behind the other axially and are separated axially from one another, each longitudinal slot 5a; 5b being axially outside at the appropriate end 6; 7 of the connecting element 1. In FIG. 8, the connecting element 1 comprises four longitudinal slots 5a; 5b; 5c; 5d, which are disposed offset from one another axially as well as on the periphery. The longitudinal slots 5a; 5b; 5c; 5d overlap axially at their ends. Furthermore, the two longitudinal slots 5a; 5d axially on the outside are closed at the end 6, 7 in question of the connecting element 1. In FIG. 9, the connecting element 1 also comprises four longitudinal slots 5a; 5b; 5c; 5d, which are separated axially from one another here and lie in the same diametrical planes. The axially external, longitudinal slots 5*a*; 5*d* are closed off at the corresponding ends 6; 7 of the connecting element 1.

Further embodiments, in turn, of the connecting element 1 are shown in FIGS. 10 to 14. The connecting element 1 may have one or more longitudinal slots 5 of one of the embodiments shown in FIGS. 4 to 9. It is evident from the cross sections, orthogonal to the longitudinal axis 2 (FIG. 4) and shown in FIGS. 10 to 14, that the connecting element 1: of FIG. 10 comprises one or more longitudinal slots 5, which penetrate the sheath 4 radially from the cavity 3 up to the external surface; of FIG. 11 comprises at least two diametrically opposite longitudinal slots 5*a*; 5*b*, penetrating the sheath 4 radially from the cavity 3 up to the external surface; of FIG. 12 comprises at least four longitudinal slots 5*a*; 5*b*; 5*c*; 5*d*, which, in pairs, penetrate the sheath 4 radially from the cavity 3 up to the external surface; of FIG. 13 comprises at least three longitudinal slots 5*a*; 5*b*; 5*c*, penetrating the sheath 4 radially from the cavity 3 up to the external surface; and of FIG. 14 comprises at least four longitudinal slots 5*a*; 5*b*; 5*c*, which are distributed uniformly on the periphery and penetrate the connecting element 1 diametrically.

Figure 15:
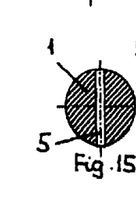
FIG. 15 shows a cross section, which is orthogonal to the longitudinal axis of a connecting element that does not have a longitudinally extending hole, with a longitudinal slot.
Figure 16:
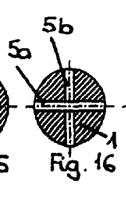
FIG. 16 shows a cross section, which is orthogonal to the longitudinal axis of a connecting element that does not have a longitudinally extending hole, with two longitudinal slots.
Figure 17:
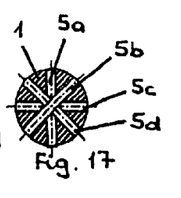
FIG. 17 shows a cross section, which is orthogonal to the longitudinal axis of a connecting element that does not have a longitudinally extending hole, with four longitudinal slots.

In FIGS. 15 to 17, different embodiments are shown, which comprise a connecting element 1 without a cavity. Here also, the connecting element 1 may comprise one or more longitudinal slots 5, similarly to one of the embodiments shown in FIGS. 4 to 9. It is evident from the cross sections, shown in FIGS. 15 to 17 and orthogonal to the longitudinal axis 2 (FIG. 4), that the connecting element 1: of FIG. 15 comprises at least one longitudinal slot 5, passing diametrically through the connecting element 1; of FIG. 16 comprises at least two longitudinal slots 5*a*; 5*b*, which are perpendicular to one another and pass through the connecting element 1 diametrically; and of FIG. 17 comprises at least four longitudinal slots 5*a*; 5*b*; 5*c*; 5*d*, which are distributed uniformly on the periphery and penetrate the connecting element 1 diametrically.

Figure 18:
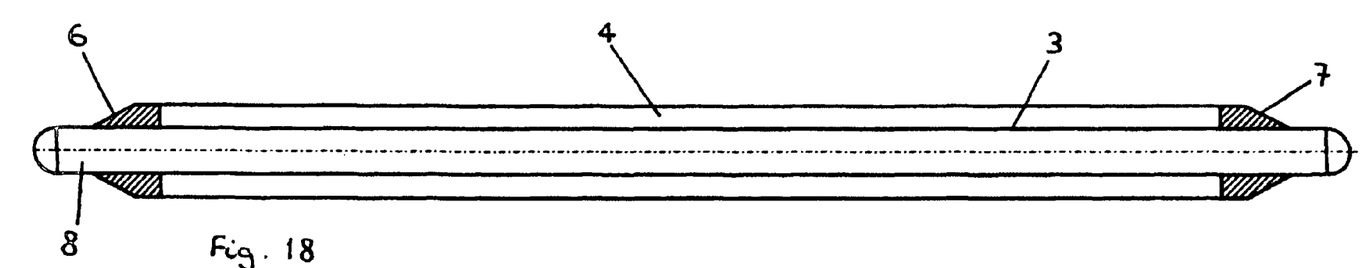
FIG. 18 shows a longitudinal section through a modified connecting element, into which a central rod has been introduced.

An embodiment of the connecting element 1 is shown in FIG. 18. It has a cavity 3 and a central rod 8, which is introduced into this cavity 3. The central rod 8 has a circularly cylindrical structure and is pushed into the cavity 3 without axial fixation.

Figure 19:
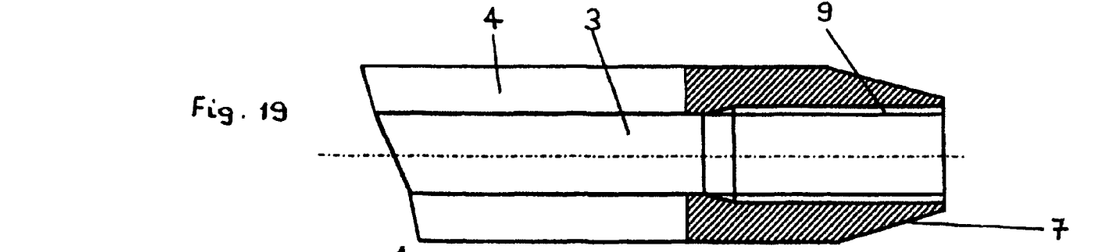
FIG. 19 shows an enlarged section of a variation of the connecting element of FIG. 18, which has an internal thread on one side.
Figure 20:
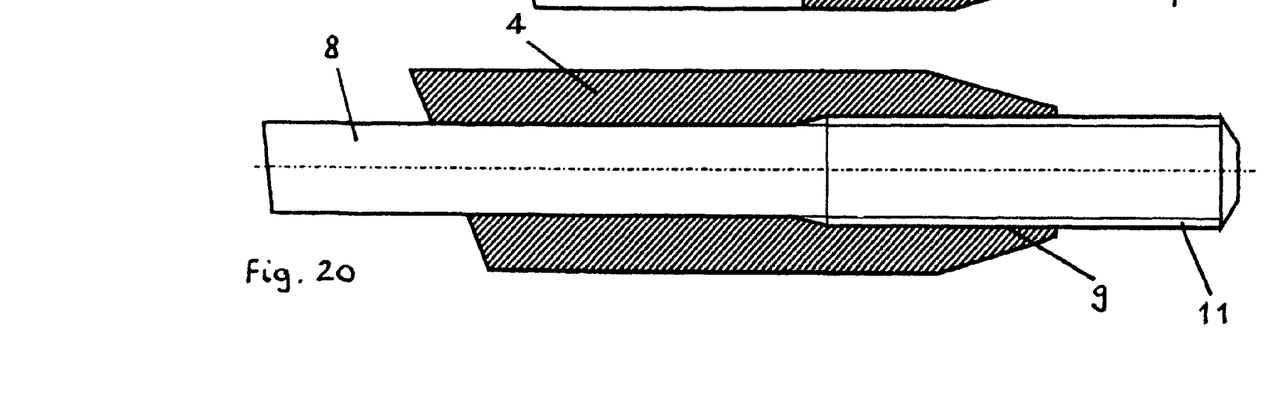
FIG. 20 shows an enlarged section of the variation of FIG. 19 with a central rod screwed into the internal thread.

FIG. 20 shows a different embodiment of a connecting element, which also has a coaxial cavity 3. At the front end 7, the coaxial cavity is provided with an internal thread 9 (FIG. 19). A central rod 8, having a complementary external thread 11, may be screwed into this internal thread 9 and can thus be fixed axially, so that the central rod 8 cannot slide unintentionally out of the connecting element 1.

Figure 21:
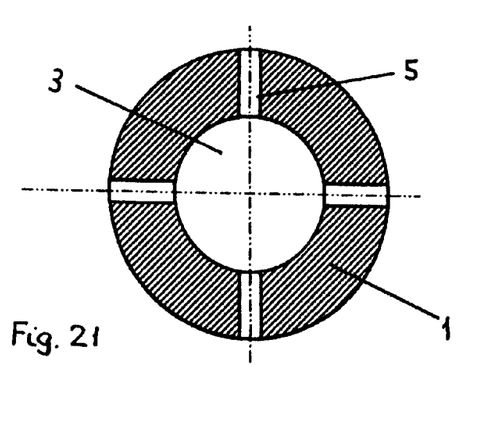
FIG. 21 shows a cross section, orthogonal to the longitudinal axis of an inventive connection element with four slots, in the not clamped state.
Figure 22:
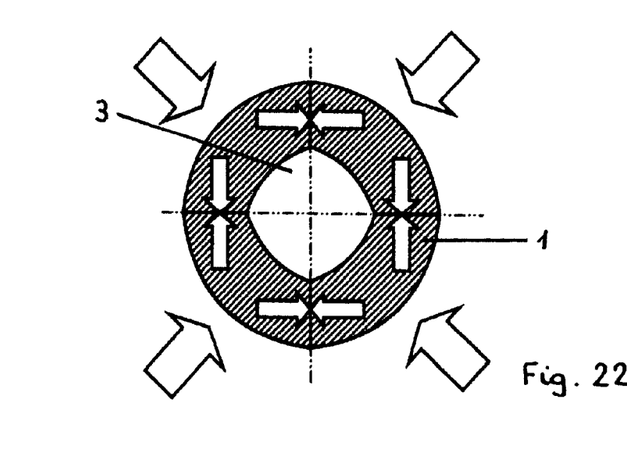
FIG. 22 shows the cross section of FIG. 21 in the clamped state, the clamping of the individual tube segments of the connecting element being indicated by arrows.

FIGS. 21 and 22 show an embodiment of the connecting element 1 with four longitudinal slots 5 and a cavity 3, which is coaxial with the longitudinal axis 2 (FIG. 1). The connecting element 1 is shown in the not clamped state in FIG. 21 and in the clamped state in FIG. 22. As shown in FIG. 22, the clamping forces, acting on the connecting element 1 and indicated by arrows, cause the individual tube segments of the connecting element 1 to be compressed until the longitudinal slots 5 are closed and the tubular segments are pressed against one another at their side walls, which form the boundaries of the longitudinal slots 5. The compressive forces, acting on the side walls of the longitudinal slots 5, are also represented by arrows.

Figure 23:
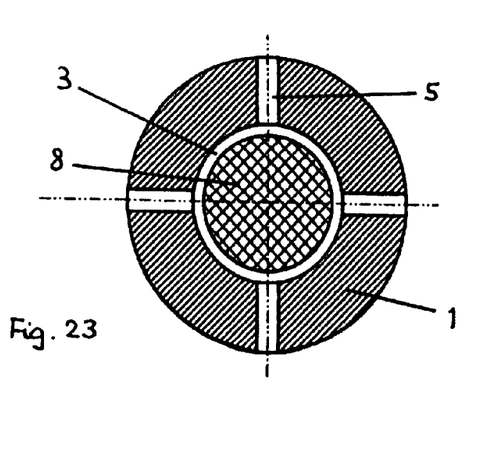
FIG. 23 shows a cross section, which is orthogonal to the longitudinal axis of an inventive connecting element with four slots and a central rod introduced therein, in the not clamped state.
Figure 24:
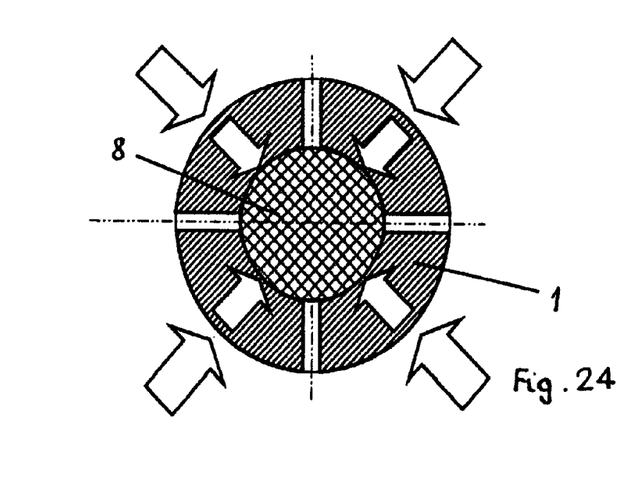
FIG. 24 shows the cross section of FIG. 23 in the clamped state, the clamping of the individual tube segments and of the central rod being indicated by arrows.

Similarly, an embodiment of the connecting element 1 with four longitudinal slots 5 and a central rod 8, introduced into the cavity 3, is shown in FIGS. 23 and 24, the connecting element 1 being shown in the not clamped state in FIG. 23 and in the clamped state in FIG. 24. The forces, acting radially on the connecting element 1 and indicated by arrows, compress the individual tube segments radially only until the wall of the cavity 3 comes into contact with the surface of the central rod 8, so that the tube segments are pressed against the central rod and the longitudinal slots are not compressed.

Figures 10, 11, 12, 13, 14:
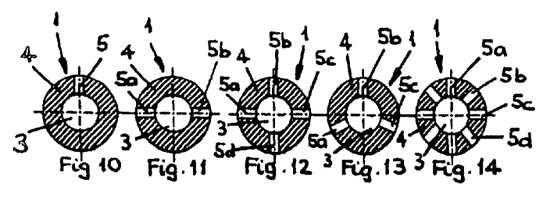
FIG. 10 shows a cross section, which is orthogonal to the longitudinal axis of a hollow connecting element, with one slot.
FIG. 11 shows a cross section, which is orthogonal to the longitudinal axis of a hollow connecting element, with two slots, which are diametrically opposite to one another.
FIG. 12 shows a cross section, which is orthogonal to the longitudinal axis of a hollow connecting element, with four uniformly disposed slots.
FIG. 13 shows a cross section, which is orthogonal to the longitudinal axis of a hollow connecting element, with three uniformly disposed slots.
FIG. 14 shows a cross section, which is orthogonal to the longitudinal axis of a hollow connecting element, with eight uniformly disposed slots.
Figure 25:
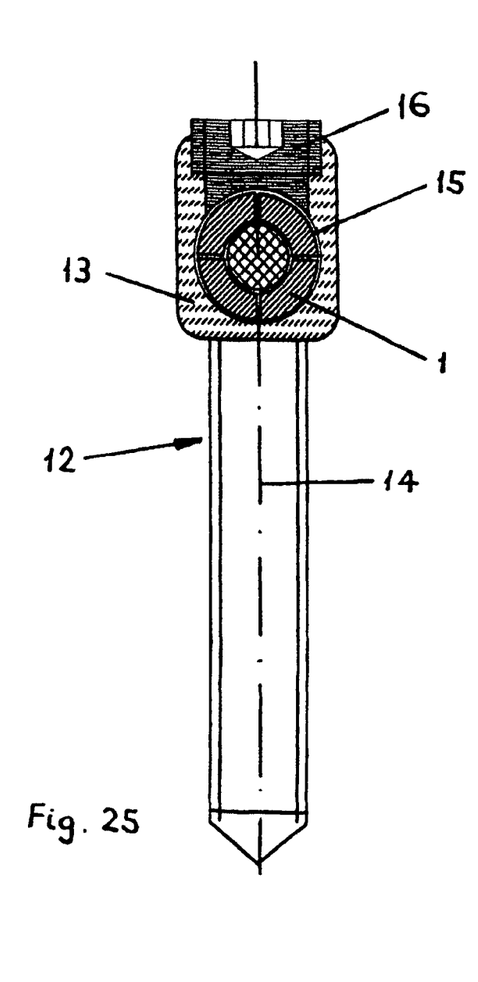
FIG. 25 shows a diagrammatic longitudinal section through a pedicle screw, into the seating head of which the connecting element with the central rod of FIG. 24 has been introduced in the not clamped state.
Figure 26:
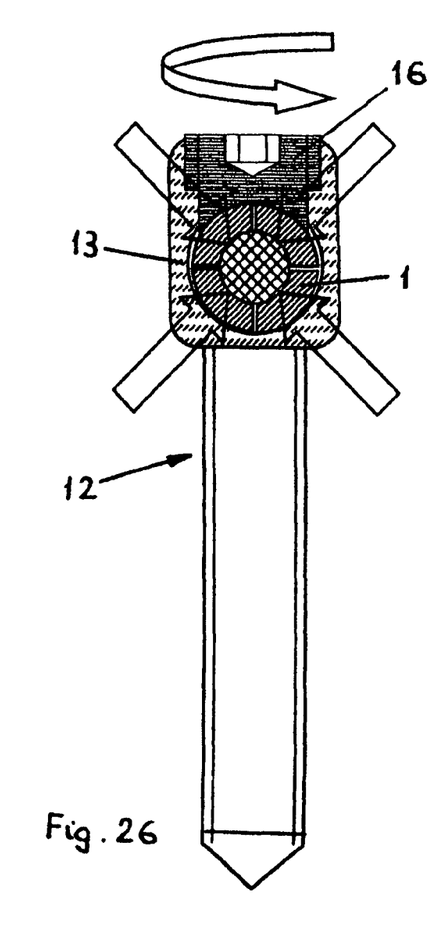
FIG. 26 shows the longitudinal section of FIG. 25 in the clamped state.
Figure 27:
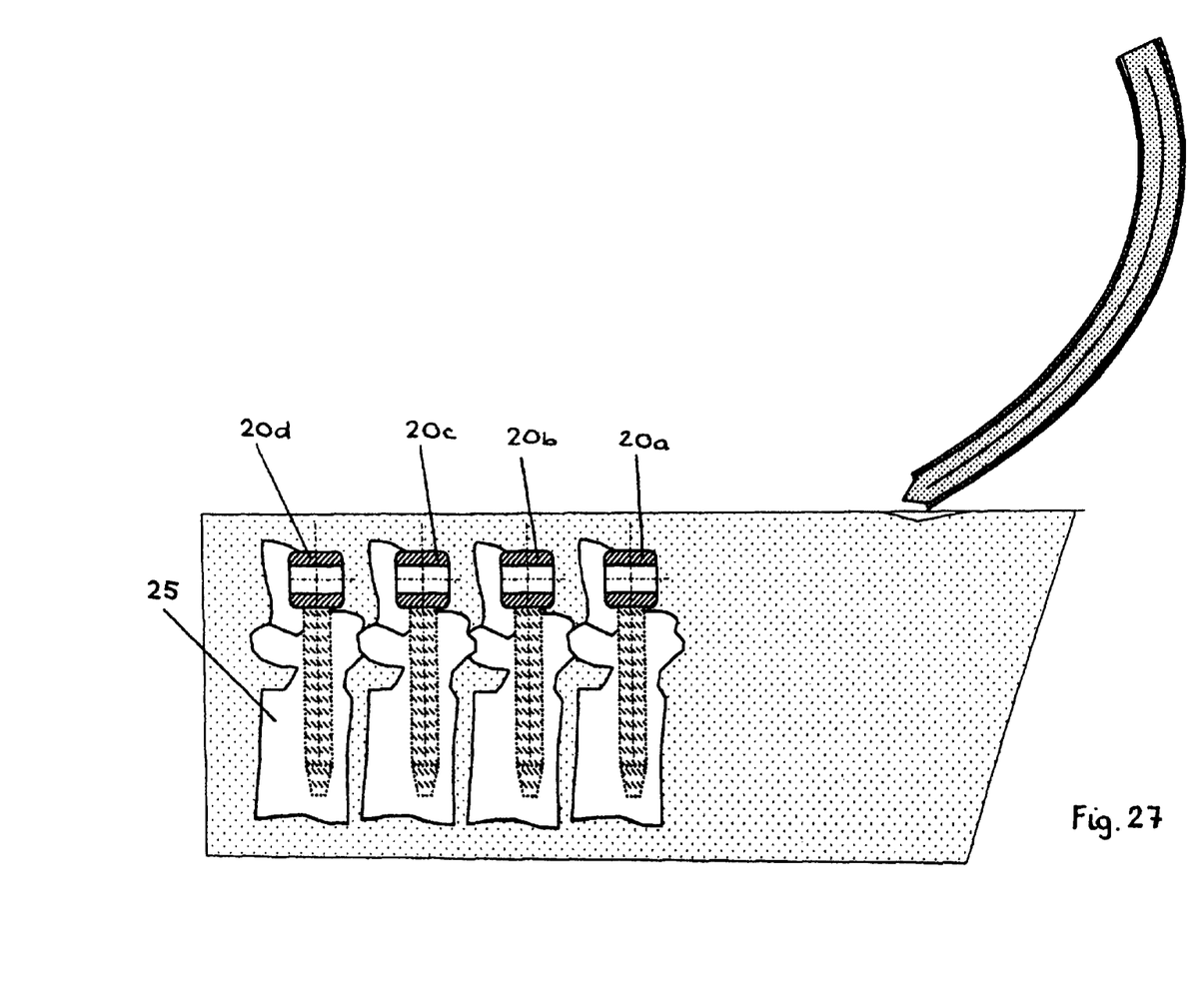
FIG. 27 shows a diagrammatic representation of a section through a spinal column with four with four implant anchoring elements introduced into adjacent vertebrae with a guiding instrument for the inventive connecting element.
Figure 28:
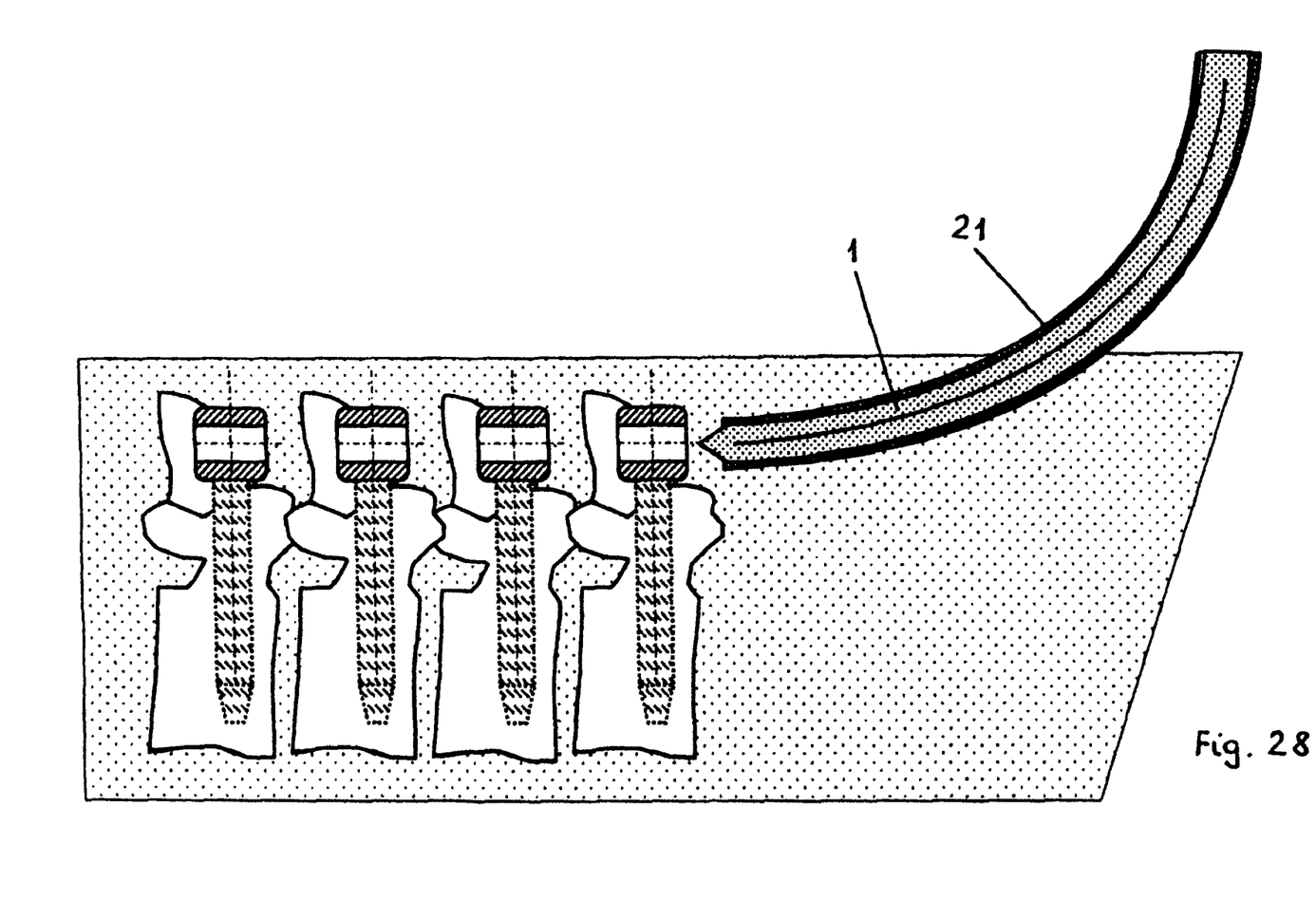
FIG. 28 shows the representation of FIG. 27 with the guiding instrument, brought into position in the vicinity of the first implant-anchoring element, with the connecting element guided therein.

FIGS. 25 and 26 show an embodiment of the connecting element 1 of FIG. 12 together with a pedicle screw 12. The connecting element 1 is placed in a channel 15, which passes through the seating head 13 of the pedicle screw 12 transversely to the central axis 14 of the latter. FIG. 25 shows the clamping screw 16, which, in the loosened state, can be screwed parallel to the central axis 14 into the seating head 13, so that the connecting element 1 can be shifted parallel to its longitudinal axis 2. In FIG. 26, the clamping screw 16 is tightened and the connecting element 1 is firmly clamped in the seating head 13 of the pedicle screw 12. The arrows represent the forces acting on the connecting element 1 during the tightening of the clamping screw 16.

The surgical technique for the inventive connecting element 1 is described briefly below.

The connecting element 1 with longitudinal slots 5 permits posterior spinal column repair with a minimally invasive surgical technique. The objective of this minimally invasive surgical technique is to implant the implant-anchoring elements 20, such as screws, hooks, jaws, etc., as well as the longitudinal support by way of minimal accesses. The flexibility of the longitudinal support enables it to be implanted by means of a curved implantation aid, such as a curved tube. With that, the surgical access is reduced to the dimensions of the tube. The implant-anchoring elements 20, lengthened by means of manipulators, enable the individual vertebrae to be manipulated during the introduction of the slotted connecting elements 1, such as the correction of the spinal column if the connecting element 1 is horizontal. After the desired correction has been achieved, the connecting element 1 is fixed in the individual implant anchoring elements 20. As a result, stiffening of the slotted connecting element 1 is achieved and sufficient stiffness of the fracture repair is attained.

Figure 29:
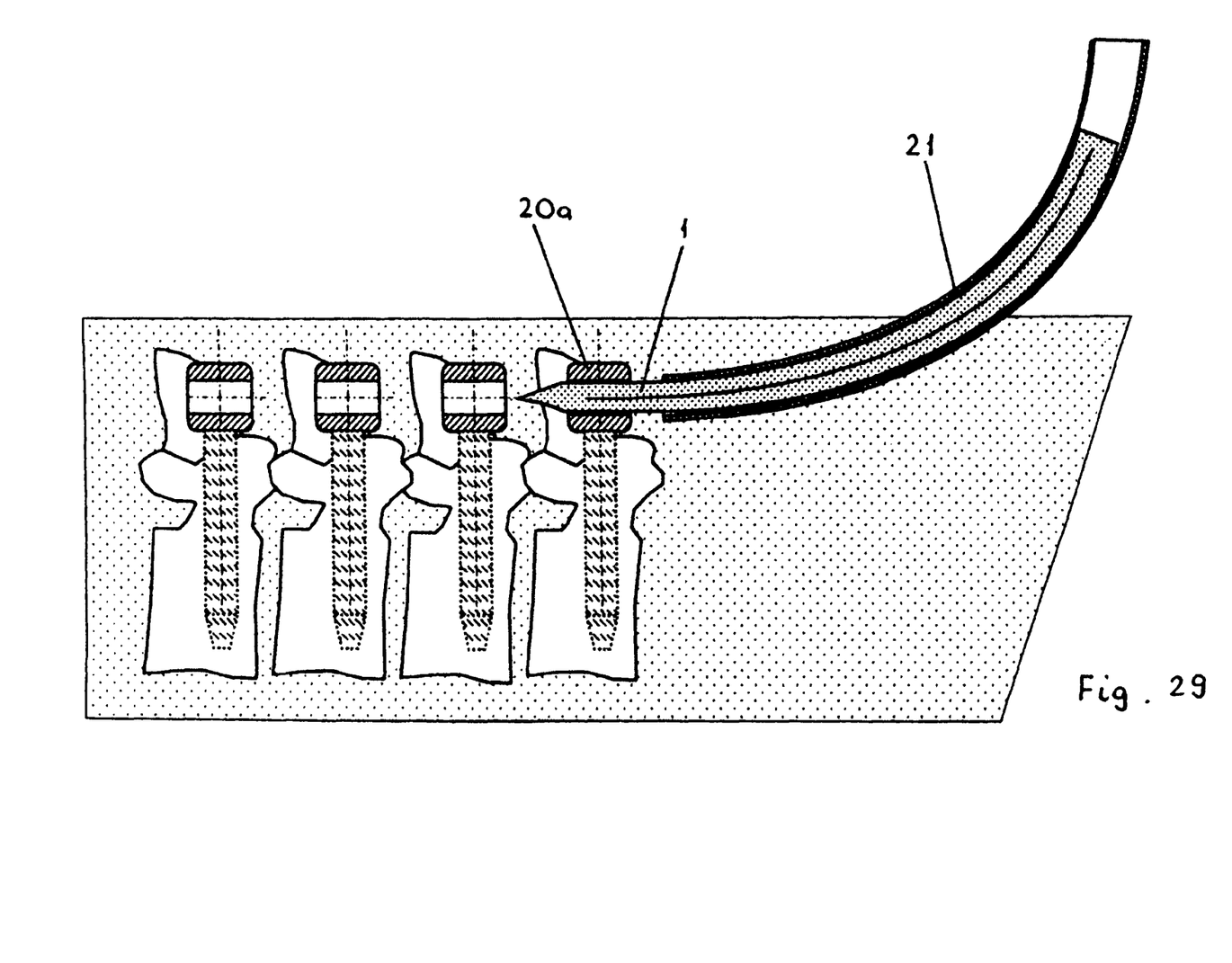
FIG. 29 shows the representation of FIG. 27 with the connecting element, introduced into the first implant-anchoring element.
Figure 30:
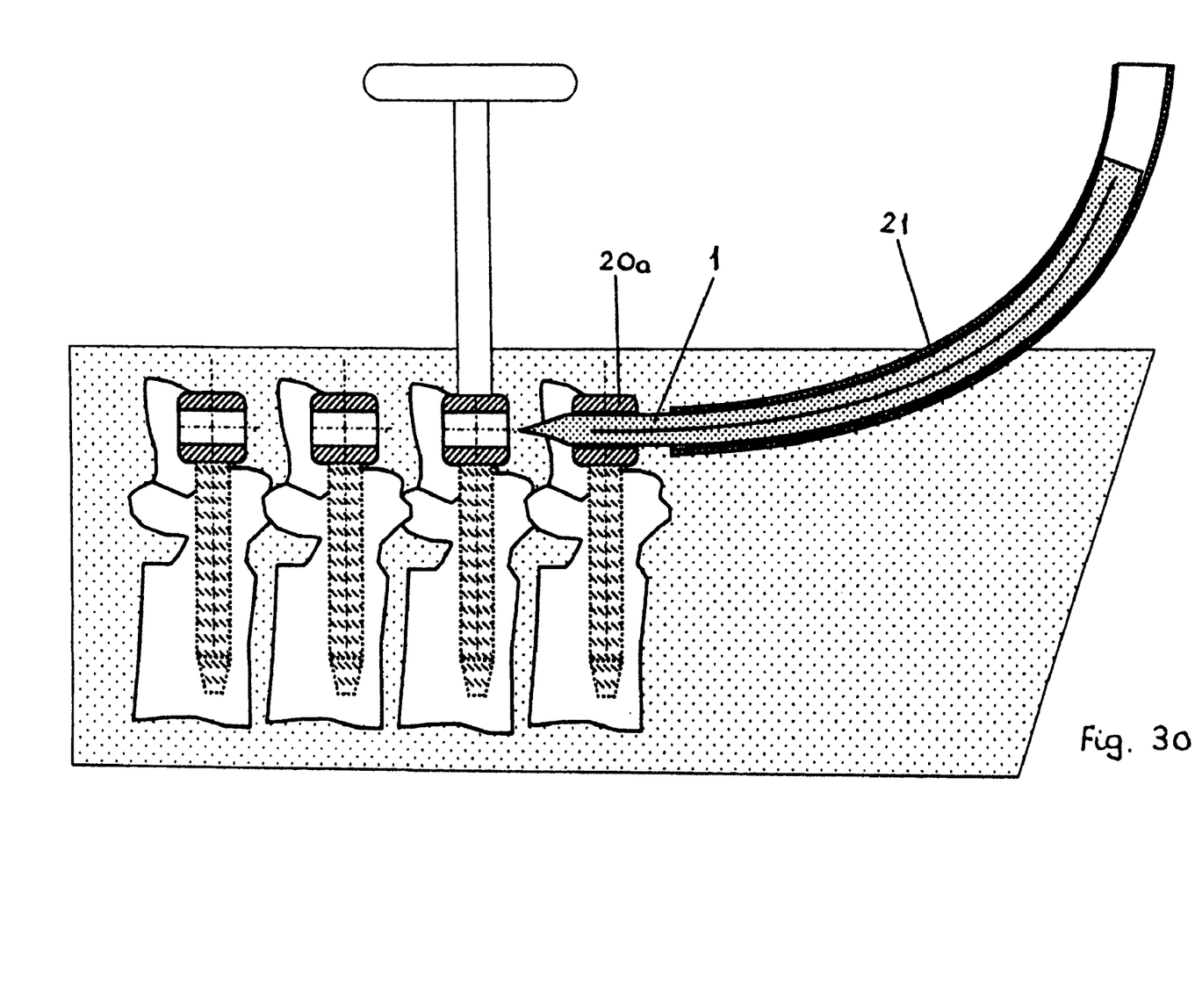
FIG. 30 shows the representation of FIG. 27 with a manipulator mounted on the second implant-anchoring element.
Figure 31:
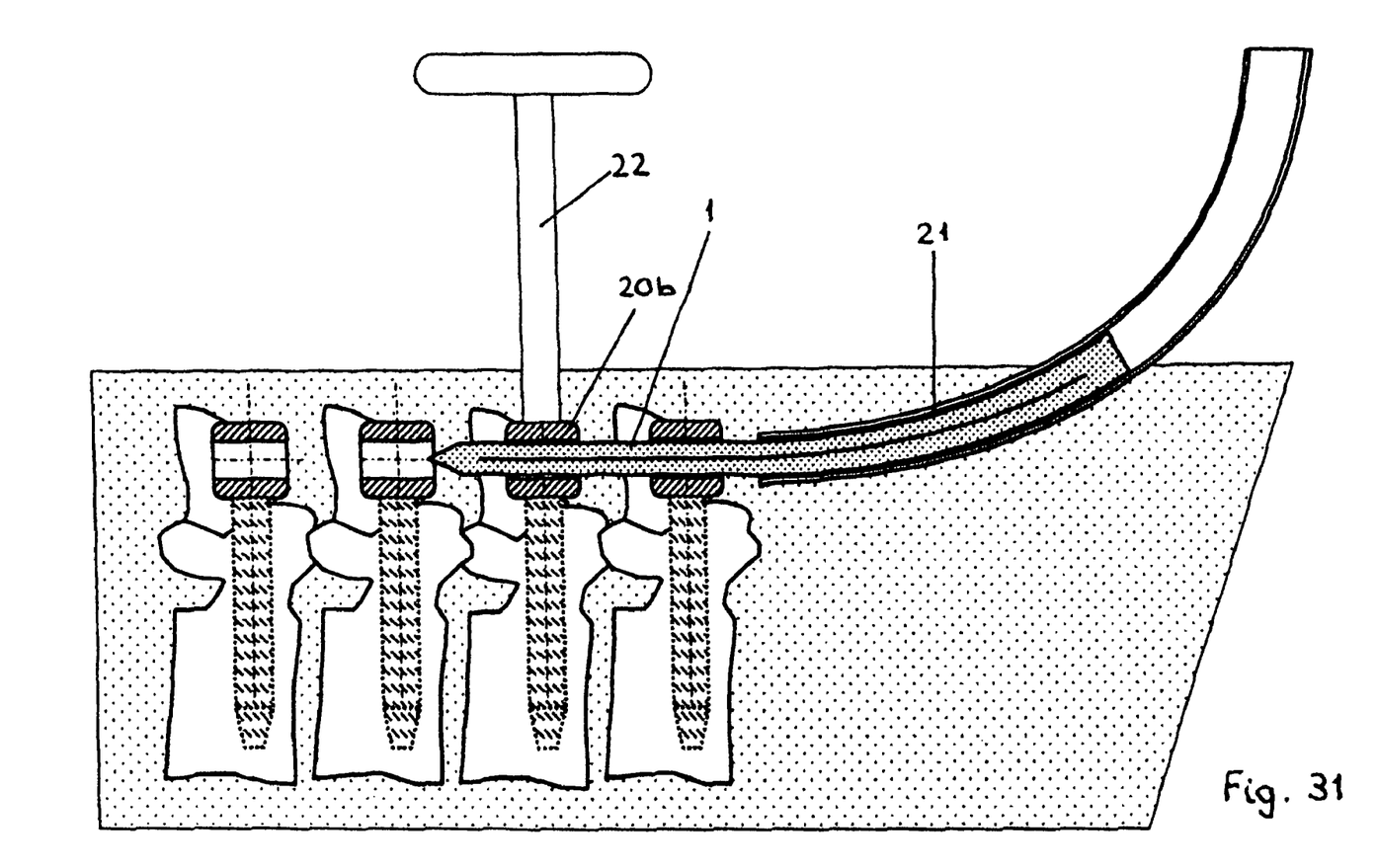
FIG. 31 shows the representation of FIG. 27 with the connecting element introduced into the first and second implant-anchoring elements.
Figure 32:
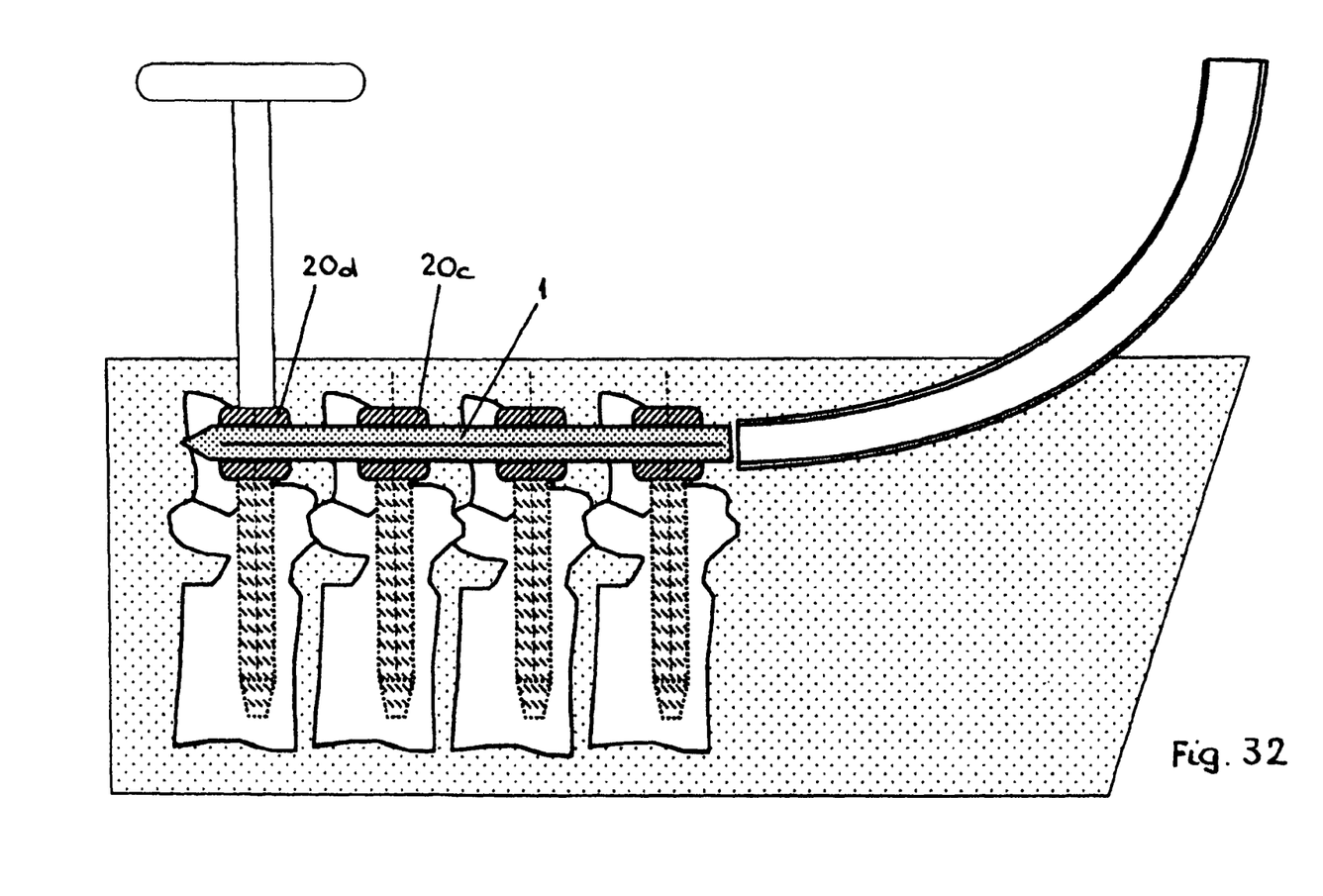
FIG. 32 shows the representation of FIG. 27 with the connecting element introduced into all four implant-anchoring elements and a manipulator for aligning the individual implant-anchoring elements.

The individual steps of the surgery are now explained in detail by means of FIGS. 27 to 34:

1. Percutaneous implantation, guided over pulling wires if necessary, of the implant-anchoring elements 20*a*; 20*b*; 20*c*; 20*d* at the vertebrae 25, which are to be treated (FIG. 27).
2. Percutaneous introduction of the guiding instrument 21 for the slotted connecting element 1 (FIG. 28).
3. Locating the first implant-anchoring element 20*a* with the guiding instrument 21 (FIG. 29). This may be accomplished over image processors or guided by way of an external targeting device, which is connected with the first implant-anchoring element 20*a*.
4. Bringing the slotted connecting element 1 by means of the guiding instrument 21 into the first implant-anchoring element 20*a* (FIG. 30).
5. Further introduction of the connecting element 1 and threading into the second implant-anchoring element 20*b* (FIG. 31). The threading may be supported by the external manipulators 22, which are connected with the implant-anchoring elements 20*b*.
6. Further introduction of the connecting element 1 and threading into the third and last implant-anchoring element 20*c*; 20*d* (FIG. 32).
7. After the connecting element 1 has been implanted in all implant-anchoring elements 20*a*; 20*b*; 20*c*; 20*d*, a desired correction of the spinal column can be made by way of the external manipulators 22 of the implant-anchoring elements 20.

Figure 33:
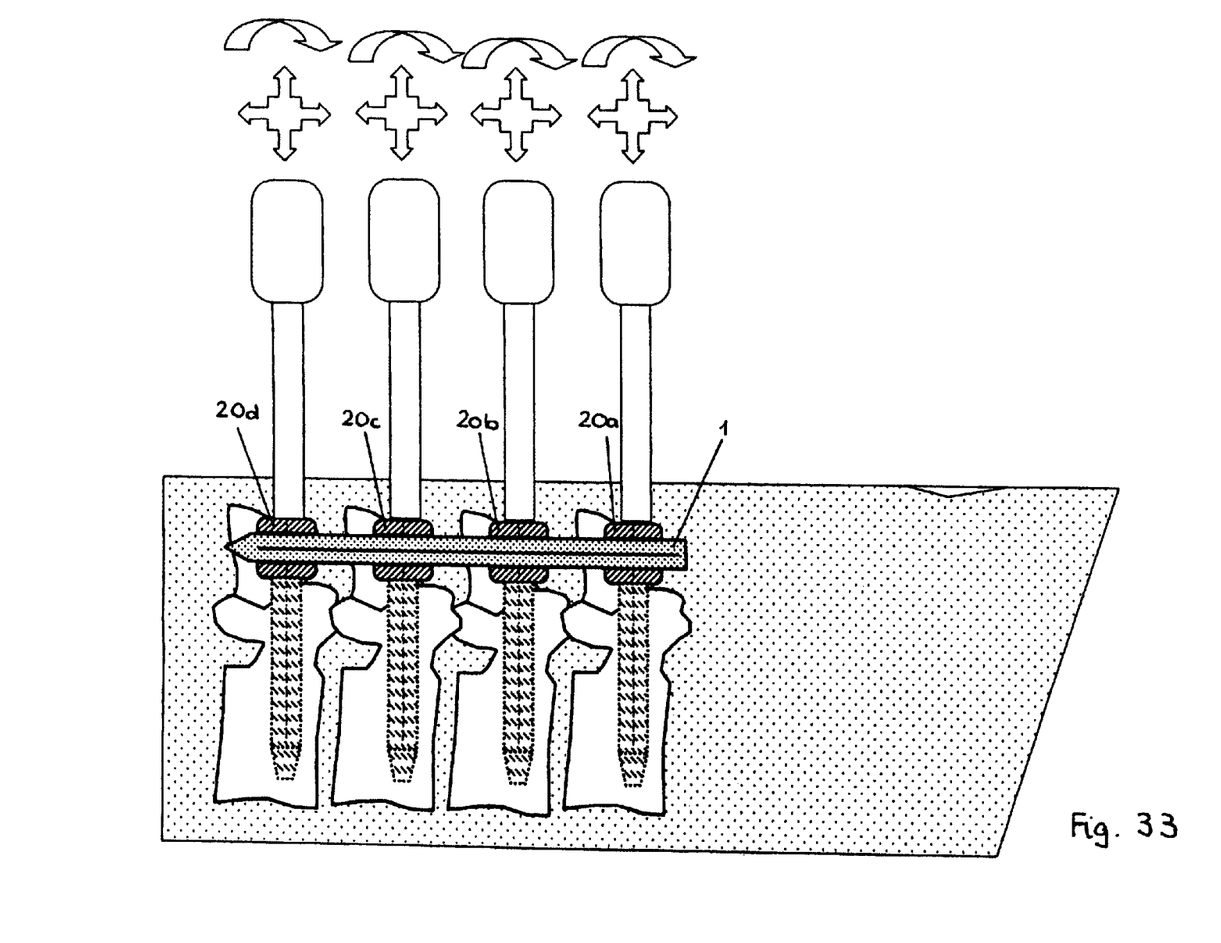
FIG. 33 shows the representation of FIG. 32 with a diagrammatic representation of the way, in which the manipulator functions
Figure 34:
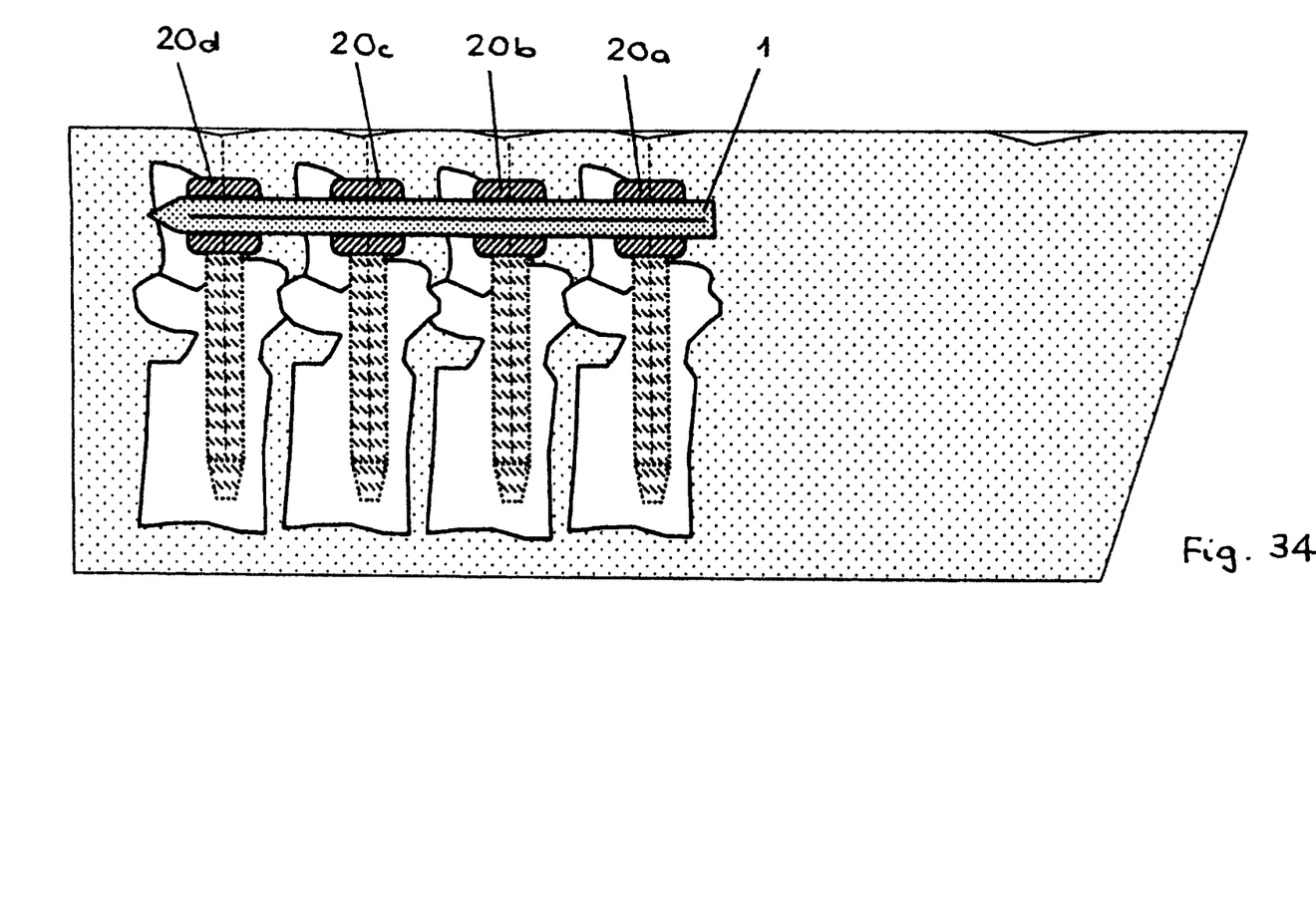
FIG. 34 shows the representation of FIG. 27 with the connecting elements, introduced into all four implant-anchoring elements and locked therein.

8. After the correction has been made, it is fixed by clamping the connecting element 1 in the individual implant-anchoring elements 20a, 20b, 20c, 20d (FIG. 33). This fixation leads to the stiffening of the connecting element 1 and makes possible a stress-resistant correction of the spinal column.

9. After removal of the guiding instrument and the anchoring manipulators (FIG. 34), the stab incision is closed off.

What is claimed:

1. A connecting element for connecting bone-anchoring elements including clamping elements, the connecting element comprising:
   a longitudinal element having an outer periphery, a longitudinal axis, a front end, a rear end, and a substantially circular cross-section;
   wherein the longitudinal element includes a plurality of longitudinal slots formed in the outer periphery and defining at least two separate cross-sectional portions of the longitudinal element, the separate cross-sectional portions having spaced apart peripheral boundaries, the longitudinal slots extending substantially parallel to the longitudinal axis of the longitudinal element;
   wherein compression by the clamping elements decreases a distance between the at least two cross-sectional portions of the longitudinal element and increases the stiffness of the longitudinal element.

2. The connecting element of claim 1, wherein the longitudinal element further comprises a cavity.

3. The connecting element of claim 2, wherein the cavity extends from the front end through to the rear end.

4. The connecting element of claim 2, wherein the cavity is configured to receive a rod.

5. The connecting element of claim 1, wherein the longitudinal element is comprised of plastic.

6. The connecting element of claim 1, wherein the longitudinal slots communicate with at least one of the front end and rear end.

7. The connecting element of claim 1, wherein the longitudinal slots have a width less than about 1.0 mm.

8. The connecting element of claim 1, wherein the longitudinal slots have a width less than about 0.6 mm.

9. The connecting element of claim 1, wherein the longitudinal slots are at least partially filled with a first material.

10. The connecting element of claim 9, wherein the first material is PEEK.

11. The connecting element of claim 9, wherein the longitudinal element is made of a second material, and wherein the first material is relatively softer than the second material.

12. A connecting system for connecting bone-anchoring elements comprising:
    a longitudinal element having an outer periphery, a longitudinal axis, a front end, a rear end, and a cavity extending along the longitudinal axis and in communication with at least one of the front end and rear end; and
    a rod inserted into the cavity;
    wherein the longitudinal element includes a plurality of longitudinal slots formed in the outer periphery and defining at least two separate cross-sectional portions of the longitudinal element, the separate cross-sectional portions having spaced apart peripheral boundaries, the longitudinal slots extending substantially parallel to the longitudinal axis of the longitudinal element;
    wherein radial compression of the longitudinal element decreases a distance between the at least two cross-sectional portions of the longitudinal element and increases the stiffness of the longitudinal element.

13. The connecting system of claim 12, wherein the rod is selectively fixable within the longitudinal element.

14. The connecting system of claim 13, wherein the rod is fixable within the longitudinal element by applying a force to the longitudinal element.

15. The connecting system of claim 12, wherein the rod is at least partially threaded.

16. The connecting system of claim 15, wherein the longitudinal element is at least partially threaded.

17. The connecting system of claim 12, wherein the longitudinal element has a substantially circular cross-section.

18. A connecting system comprising:
    a longitudinal element having an outer periphery, a longitudinal axis, a front end, a rear end, and a plurality of longitudinal slots formed in the outer periphery and defining at least two separate cross-sectional portions of the longitudinal element, the separate cross-sectional portions having spaced apart peripheral boundaries, the longitudinal slots extending substantially parallel to the longitudinal axis of the longitudinal element; and
    a first bone anchoring element having a channel for receiving the longitudinal element therethrough;
    wherein the longitudinal element is compressible by manipulation of the first bone anchoring element to decrease a distance between the at least two cross-sectional portions of the longitudinal element and increase the stiffness of the longitudinal element.

19. The connecting system of claim 18, wherein the first bone anchoring element includes a pedicle screw.

20. The connecting system of claim 18, wherein the first bone anchoring element includes a clamping screw for engagement with the longitudinal element.

21. The connecting system of claim 18, further comprising a second bone anchoring element having a second channel for receiving the longitudinal element therethrough.

22. The connecting system of claim 18, wherein the longitudinal slots are deformable by manipulation of the first bone anchoring element.

23. The connecting system of claim 18, wherein the longitudinal slots have a width, and wherein the width is decreased by manipulation of the first bone anchoring element.

24. A connecting element for connecting bone anchoring elements comprising:
    a longitudinal element having an outer periphery, a longitudinal axis and a plurality of longitudinal slots formed in the outer periphery, the longitudinal slots extending parallel to the longitudinal axis of the longitudinal element and defining at least two separate cross-sectional portions of the longitudinal element, the separate cross-sectional portions having spaced apart peripheral boundaries, the longitudinal element including a first configuration in which the longitudinal element is relatively flexible, and a second, compressed configuration wherein a distance between the at least two cross-sectional portions of the longitudinal element is decreased and in which the longitudinal element is relatively inflexible.

25. The connecting element of claim 24, wherein the longitudinal slots are disposed radially around the perimeter of the longitudinal element.

26. The connecting element of claim 24, wherein the longitudinal element has a substantially circular cross-section.

27. The connecting element of claim 24, wherein the longitudinal element has a substantially polygonal cross-section.

28. The connecting element of claim 24, wherein the longitudinal slots are at least partially filled with a first material.

29. The connecting element of claim 28, wherein the material is PEEK.

30. The connecting element of claim 28, wherein the first longitudinal element is made of a second material, and wherein the first material is relatively softer than the second material.

31. The connecting element of claim 24, wherein the longitudinal element further comprises a cavity configured to receive a rod.

32. The connecting element of claim 24, wherein the longitudinal element is comprised of plastic.

33. A connecting element for connecting bone anchoring elements comprising:
- a longitudinal element having an outer periphery, a longitudinal axis, and a plurality of longitudinal slots formed in the outer periphery, each longitudinal slot extending substantially parallel to the longitudinal axis of the longitudinal element and includes a width separating at least two cross-sectional portions of the longitudinal element, the cross-sectional portions having spaced apart peripheral boundaries;
- wherein the width of each longitudinal slot is configured to be decreased after the longitudinal element is implanted causing the two cross-sectional portions of the longitudinal element to move toward each other.

34. The connecting element of claim 33, wherein the width of each longitudinal slot is decreased due to a clamping force.

35. The connecting element of claim 33, wherein the width of each longitudinal slot is decreased to approximately zero.

36. The connecting element of claim 33, wherein the width of each longitudinal slot is less than about 1.0 mm.

37. The connecting element of claim 33, wherein the width of each longitudinal slot is less than about 0.6 mm.

38. The connecting element of claim 33, wherein the width of each longitudinal slot is decreased by the manipulation of a bone anchoring element.

39. The connecting element of claim 38, wherein the manipulation of the bone anchoring element includes displacing a clamping screw.

40. The connecting element of claim 33, wherein the longitudinal slots are at least partially filled with a first material.

41. The connecting element of claim 40, wherein the first material is PEEK.

42. The connecting element of claim 40, wherein the longitudinal element is made of a second material, and wherein the first material is relatively softer than the second material.

43. A connecting element for connecting bone anchoring elements comprising:
- a longitudinal element having an outer periphery, a longitudinal axis, an outer diameter and a plurality of longitudinal slots formed in the outer periphery, each longitudinal slot extending parallel to the longitudinal axis of the longitudinal element and defining at least two separate cross-sectional portions of the longitudinal element, the separate cross-sectional portions having spaced apart peripheral boundaries; and
- wherein the outer diameter is configured to be decreased after the longitudinal element is implanted by decreasing a distance between the at least two cross-sectional portions.

44. The connecting element of claim 43, wherein the longitudinal slots are disposed radially around the perimeter of the longitudinal element.

45. The connecting element of claim 43, wherein the longitudinal element further has an inner diameter.

46. The connecting element of claim 45, wherein inner diameter is configured to be decreased after the longitudinal element is implanted.

47. The connecting element of claim 43, wherein the longitudinal element has a substantially circular cross-section.

48. The connecting element of claim 43, wherein the outer diameter is decreased by the manipulation of a bone anchoring element.

49. The connecting element of claim 48, wherein the manipulation of the bone anchoring element includes displacing a clamping screw.

50. A method of connecting bone anchoring elements comprising the steps of:
- (a) implanting first and second bone anchoring elements into bone, the first bone anchoring element having a first channel and a first clamping element, and the second bone anchoring element having a second channel and a second clamping element;
- (b) inserting a longitudinal element into the first and second channels, the longitudinal element including an outer periphery, a longitudinal axis and a plurality of longitudinal slots formed in the outer periphery, each longitudinal slot extending parallel to the longitudinal axis of the longitudinal element and defining at least two separate cross-sectional portions of the longitudinal element, the separate cross-sectional portions having spaced apart peripheral boundaries; and
- (c) manipulating the first and second clamping elements to deform the longitudinal slots and decrease a distance between the at least two cross-sectional portions of the longitudinal element.

51. The method of claim 50, wherein the longitudinal element is implanted using a guiding instrument.

52. The method of claim 50, wherein step (b) includes threadably engaging the longitudinal element with at least one of the first and second bone anchoring elements.

53. The method of claim 50, wherein step (c) includes displacing a clamping screw.

54. The method of claim 50, wherein the longitudinal element is more flexible in step (a) than after the completion of step (c).

55. The method of claim 50, wherein the longitudinal element is more flexible in step (b) than after the completion of step (c).

56. A method of connecting bone anchoring elements comprising the steps of:
- (a) implanting first and second bone anchoring elements into bone, the first bone anchoring element having a first channel, and the second bone anchoring element having a second channel;
- (b) inserting a longitudinal element in a relatively flexible configuration into the first and second channels, the longitudinal element including an outer periphery, a longitudinal axis and a plurality of longitudinal slots formed in the outer periphery, each longitudinal slot extending parallel to the longitudinal axis of the longitudinal element and defining at least two separate cross-sectional portions of the longitudinal element, the separate cross-sectional portions having spaced apart peripheral boundaries; and
- (c) manipulating the first and second bone anchoring elements to place the longitudinal element in a relatively inflexible configuration by compressing the longitudinal element and decreasing a distance between the at least two cross-sectional portions of the longitudinal element.

57. The method of claim 56, wherein step (c) includes displacing a clamping screw.

* * * * *